(12) United States Patent
Filar (10) Patent No.: US 8,262,221 B2
(45) Date of Patent: Sep. 11, 2012

(54) OPHTHALMOLOGICAL DIAGNOSTIC SYSTEM

(76) Inventor: Paul A. Filar, Sturgeon Bay, WI (US)

( * ) Notice: Subject to any disclaimer, the term of this patent is extended or adjusted under 35 U.S.C. 154(b) by 22 days.

(21) Appl. No.: 12/973,522

(22) Filed: Dec. 20, 2010

(65) Prior Publication Data

US 2011/0085138 A1  Apr. 14, 2011

Related U.S. Application Data

(63) Continuation-in-part of application No. 12/386,912, filed on Apr. 24, 2009, now Pat. No. 7,883,210.

(51) Int. Cl.
*A61B 3/14* (2006.01)
*A61B 3/10* (2006.01)
*A61B 3/00* (2006.01)

(52) U.S. Cl. .................. 351/206; 351/205; 351/245

(58) Field of Classification Search .......... 351/200, 351/203, 205, 206, 221, 222, 243–245
See application file for complete search history.

(56) References Cited

U.S. PATENT DOCUMENTS

| | | | |
|---|---|---|---|
| 4,592,631 A | 6/1986 | Nakane | |
| 5,479,222 A | 12/1995 | Volk | |
| 5,713,047 A | 1/1998 | Kohayakawa | |
| 6,168,274 B1 * | 1/2001 | Matthews | 351/221 |
| 6,393,431 B1 | 5/2002 | Salvati et al. | |
| 2002/0131633 A1 * | 9/2002 | Zwick et al. | 382/152 |
| 2005/0110949 A1 | 5/2005 | Goldfain et al. | |
| 2005/0237486 A1 | 10/2005 | Su et al. | |
| 2007/0255119 A1 * | 11/2007 | Mordaunt et al. | 600/300 |
| 2009/0307328 A1 | 12/2009 | Nuttall et al. | |

OTHER PUBLICATIONS

Heine Video Omega 2C, available at http://www.heine.com/eng_US/PRODUCTS/PRODUCT-OVERVIEW/Ophthalmic-Instruments/Indirect-Ophthalmoscopes/HEINE-Video-OMEGA-2C-R.
TotalExam S-Video Examination Camera, GlobalMedia Group, LLC., available at http://www.globalmedia.com/telemedicine/totalexam.html.

* cited by examiner

*Primary Examiner* — Thomas K Pham
*Assistant Examiner* — Brandi Thomas
(74) *Attorney, Agent, or Firm* — Absolute Technology Law Group LLC (57) ABSTRACT

The present invention is an ophthalmological diagnostic system adapted for use in urgent care facilities, physicians' offices, hospitals, mobile treatment facilities, and in remote areas. The ophthalmological diagnostic system includes a component for securely holding a digital camera in optical communication with an ophthalmoscope and in various embodiments may include hardware and software for analysis and storage of images or video captured using the ophthalmological diagnostic system. The ophthalmological diagnostic system facilitates viewing of images and video by a single diagnostician or multiple diagnosticians.

17 Claims, 9 Drawing Sheets

OPHTHALMOLOGICAL DIAGNOSTIC SYSTEM

CROSS-REFERENCE TO RELATED APPLICATIONS

This application is a continuation-in-part application that claims priority to U.S. Nonprovisional application Ser. No. 12/386,912 filed on Apr. 24, 2009 now U.S. Pat. No. 7,883,210, and herein incorporated by reference.

FIELD OF INVENTION

The present invention relates to the field of ophthalmology and more particularly to an ophthalmological diagnostic system.

GLOSSARY

As used herein, the term "in optical communication" means two or more devices perceiving the same image. For example, a digital camera in optical communication with an ophthalmoscope is capable of capturing the image as viewed by the ophthalmoscope.

As used herein, the term "optical communication housing" refers to a component that holds a device in optical communication with one or more devices.

As used herein, the term "image viewing means" refers to a device with an interface capable of displaying an image, video, or other digital representation.

As used herein, the term "camera activating means" refers to a component that signals a camera to capture an image or video.

As used herein, the term "storage component" refers to a hardware device capable of storing image data including, but not limited to a computer hard drive, database, memory card, flash drive, and an external hard drive.

As used herein, the term "grasping component" refers to a protuberance, contour, handle, or another part designed to be gripped by a hand to aid in the removal of one component from another.

As used herein, the term "diagnostician" refers to optometrists, ophthalmologists, and other individuals who are trained to analyze and identify conditions of the eye.

As used herein, the term "ophthalmological image recipient" refers to an individual who receives an image or video captured using an ophthalmological diagnostic system described herein for purposes of diagnosing or documenting an ophthalmological condition. Ophthalmological image recipients may include but are not limited to optometrists, ophthalmologists, physicians, physician assistants, medical personnel, medical and optometry students, technical and non-technical personnel, administrative personal, and any other individuals who may be involved in diagnosing or documenting an ophthalmological condition.

As used herein, the term "field of view" refers to the area or solid angle which can be viewed through an optical instrument, such as an ophthalmoscope.

As used herein, the term "filter" refers to a colored lens used to enhance a particular characteristic of an eye.

BACKGROUND

Ophthalmoscopes and slit lamps used to view the anterior segments and retina of an eye are known in the art. The WELCH ALLYN PANOPTIC ophthalmoscope is one example. The WELCH ALLYN PANOPTIC ophthalmoscope provides a panoramic view larger than standard ophthalmoscopes allowing the doctor to observe and identify conditions, such as hypertension, diabetic retinopathy, and papilledema.

When a disease or abnormality is observed, it is desirable to document the image that is visible in a photograph and/or video. Such documentation is important for diagnosis, as well as for comparison purposes and patient education. Ophthalmoscopes and slit lamps known in the art do not allow the doctor to capture the image, requiring that a second piece of equipment be used (e.g., a retinal camera). In an office setting, there are typically multiple machines that are used for photographing the eye. For example, there will be one machine designated for photographing the front of an eye and a second machine designated for photographing the back of an eye. When a patient is being seen in an out-of-office setting, such as a nursing home, it is impractical for the doctor to transport the bulky and expensive equipment required to both view and photograph the eye.

Camera equipment known in the art is undesirable for a number of reasons. The large size and bulkiness of existing optical cameras make them impractical to transport. In addition, these optical cameras lack the ability to photograph both the anterior and retina of a patient's eye, have a limited field of view, require a flash or a beam splitter to separate the optics, are clumsy to use, and/or take photographs of poor quality.

Ophthalmoscopes with digital documenting capabilities are known in the art. One is example is disclosed in U.S. Publication No. 2005/0110949 A1 (Goldfain et al.). Goldfain et al. teaches an eye viewing device with an imaging element that allows a practitioner to view an eye and sequentially image the same region of the eye for recording, documentation, and/or analysis. Another example is disclosed in U.S. Pat. No. 6,393,431 (Salvati et al.). Salvati et al. teaches an imaging instrument with a plurality of interchangeable instrument heads with an optical system capable of capturing and storing images and videos.

The devices taught by Goldfain et al. and Salvati et al. are not desirable because they are not capable of securing a digital camera to an existing ophthalmoscope without requiring alteration to the ophthalmoscope and allowing the digital camera to be subsequently removed from the ophthalmoscope so that it can be used without the digital camera. In addition, these devices are very costly.

GlobalMedia Group, LLC is one example of a company that provides telemedicine services and telemedicine hardware and software that allow healthcare providers to communicate with healthcare providers in other locations. One example of telemedicine hardware provided by GlobalMedia is the TOTALEXAM examination camera. The TOTALEXAM examination camera is a hand-held camera capable of capturing images in healthcare and non-healthcare settings. While the devices and services provided by GlobalMedia allow healthcare professionals to communicate with other healthcare professionals, the devices and services provided by GlobalMedia are not desirable for vision care.

It is desirable to have an apparatus capable of securely holding a digital camera and an ophthalmoscope in optical communication.

It is desirable to have an apparatus for holding a digital camera in optical communication with an ophthalmoscope allowing the anterior segment and retina of an eye to be photographed.

It is desirable to have an apparatus for holding a digital camera in optical communication with an ophthalmoscope that can be used with an existing ophthalmoscope without requiring alteration of the ophthalmoscope.

It is desirable to have an apparatus for holding a digital camera in optical communication with an ophthalmoscope that is compact, and makes efficient use of time and current technology.

It is desirable to have an ophthalmologic diagnostic system that is portable and specifically designed to be used in the field.

It is desirable to have an ophthalmologic diagnostic system that utilizes digital photography, video, and computer software for patient ocular care and quality medical records.

SUMMARY OF THE INVENTION

The present invention is an ophthalmological diagnostic system comprised of an optical communication housing for holding a digital camera in optical communication with an ophthalmoscope, a digital camera, an ophthalmoscope, and a computer. The optical communication housing houses a digital camera and fits securely over an ophthalmoscope, securely holding the digital camera in the proper position for digitally capturing the image visible through the ophthalmoscope.

The ophthalmological diagnostic system allows the user to communicate with diagnosticians for telemedicine purposes, and is specifically designed for use by anyone, including optometrists and ophthalmologists, in non-office settings, remote areas, anywhere traditional ophthalmological cameras are not available, or when communication with specialists for telemedicine purposes is desirable.

DETAILED DESCRIPTION OF INVENTION

For the purpose of promoting an understanding of the present invention, references are made in the text to exemplary embodiments of an ophthalmologic diagnostic system, only some of which are described herein. It should be understood that no limitations on the scope of the invention are intended by describing these exemplary embodiments. One of ordinary skill in the art will readily appreciate that alternate but functionally equivalent components, materials, designs, and equipment may be used. The inclusion of additional elements may be deemed readily apparent and obvious to one of ordinary skill in the art. Specific elements disclosed herein are not to be interpreted as limiting, but rather as a basis for the claims and as a representative basis for teaching one of ordinary skill in the art to employ the present invention.

It should be understood that the drawings are not necessarily to scale; instead, emphasis has been placed upon illustrating the principles of the invention. In addition, in the embodiments depicted herein, like reference numerals in the various drawings refer to identical or near identical structural elements.

Moreover, the terms "substantially" or "approximately" as used herein may be applied to modify any quantitative representation that could permissibly vary without resulting in a change in the basic function to which it is related.

Figure 1A:
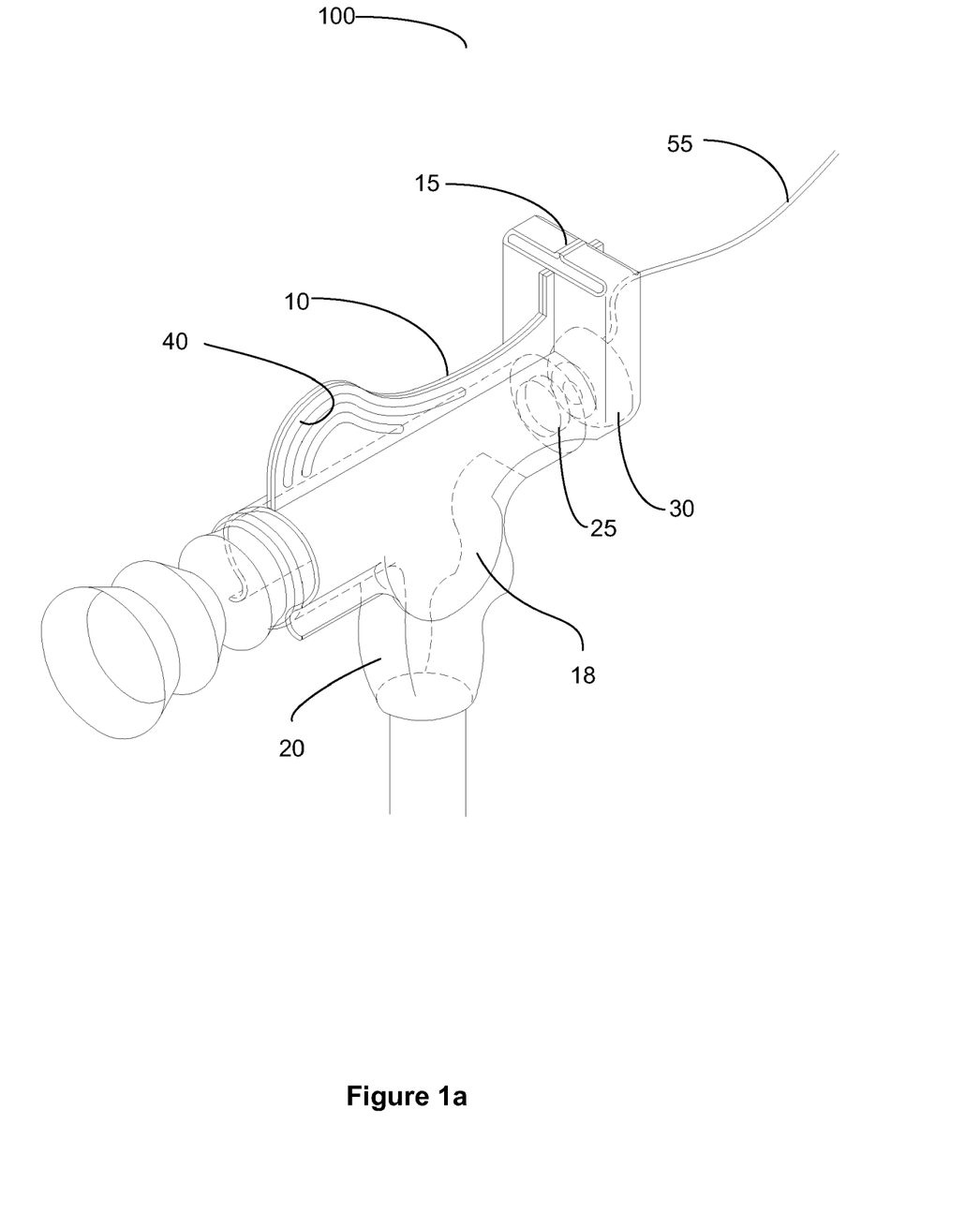
FIG. 1a illustrates a perspective view of an exemplary embodiment of an ophthalmological diagnostic system.

FIG. 1a illustrates a perspective view of an exemplary embodiment of ophthalmological diagnostic system 100 comprised of optical communication housing 10, digital camera 30, and ophthalmoscope 20. Optical communication housing 10 houses digital camera 30 and is contoured to fit securely around ophthalmoscope 20.

Optical communication housing 10 is secured to ophthalmoscope 20 by sliding optical communication housing 10 over ophthalmoscope 20 and snapping it down. When optical communication housing 10 is secured to ophthalmoscope 20, digital camera 30 is positioned and held at the precise angle that places digital camera 30 in optical communication with ophthalmoscope 20, providing an uninterrupted line of vision from digital camera 30 to the patient's eye. Visible in FIG. 1a is interface 25, the interface between ophthalmoscope 20 and digital camera 30.

In the embodiment shown, ophthalmoscope 20 is a direct ophthalmoscope with a field of view of 25 degrees; however, in various other embodiments, ophthalmoscope 20 may be a direct or indirect ophthalmoscope, a scanning laser ophthalmoscope, or any other type of ophthalmoscope known in the art and may have a field of view ranging from 6.5 to 60 degrees. In various other embodiments, ophthalmoscope diagnostic system 100 may incorporate other technologies, such as optical coherence tomography (OCT), GDX nerve fiber analyzer (Laser Diagnostic Technologies, San Diego, Calif.), or any other technology known in the art for examining the eye.

In various embodiments, ophthalmoscope 20 may further include one or more filters or additional lens for enhancing or magnifying the image viewed by ophthalmoscope 20. For example, ophthalmoscope 20 may include a red-free filter, a cobalt blue filter, a yellow filter, a slit aperture, a half-moon aperture, varying aperture sizes, a corneal viewing lens, and/or any other filter, lens, or component known in the art. In still other embodiments, the software may further include filters or other enhancement features, including but not limited to red-free filters, staining, overlays, magnification, pixel sampling, and measuring. In various embodiments, ophthalmological diagnostic system 100 may utilize software having analysis, enhancement, and/or image management capabilities known in the art, such as CAPSURE (GlobalMedia Group, LLC).

In the embodiment shown, optical communication housing 10 further includes snapshot button 15 for taking photographs or video depending on the setting selected. In the embodiment shown, snapshot button 15 is comprised of flexible pieces of optical communication housing 10 that are squeezed to take a photograph or video. In other embodiments, snapshot button 15 may protrude from optical communication housing 10, be positioned outside of optical communication housing 10, or be any other selection means that allows the user to take photographs or video.

In various other embodiments, digital camera 30 is not activated by pressing snapshot button 15, but rather may be voice-activated or activated using a foot pedal, key stroke, mouse click, touch screen (e.g., if a viewing screen is used), or by any other means known in the art.

In the embodiment shown, optical communication housing 10 is angled to fit snugly around ophthalmoscope 20 and includes side plates 18, which help to securely hold optical communication housing 10 on ophthalmoscope 20. In the embodiment shown, side plates 18 are rounded; however, in other embodiments, side plates 18 may be square, rectangular, angled, or any other shape that helps hold optical communication housing 10 in place.

Optical communication housing 10 further includes grasping component 40 which aids in the removal of optical communication housing 10 from ophthalmoscope. In the embodiment shown, grasping component 40 is fin-shaped, protrudes from the top of optical communication housing 10, and has a plurality of ridges that make grasping component 40 easier to grasp.

Also visible is USB cable 55, which connects digital camera 30 to computer 50 (not shown).

In an exemplary embodiment, optical communication housing 10 is comprised of a weather and impact resistant vacuum forming ABS plastic, and is molded as two halves and integrated together. The lack of removable or interchangeable parts results in a device that is extremely durable. In other embodiments, optical communication housing 10 may be comprised of another type of plastic or other material, such as resin, aluminum or any other material capable of holding digital camera 30 in optical communication with ophthalmoscope 20, and may be manufactured as a single piece or using another method known in the art, such as injection molding.

Figure 1B:
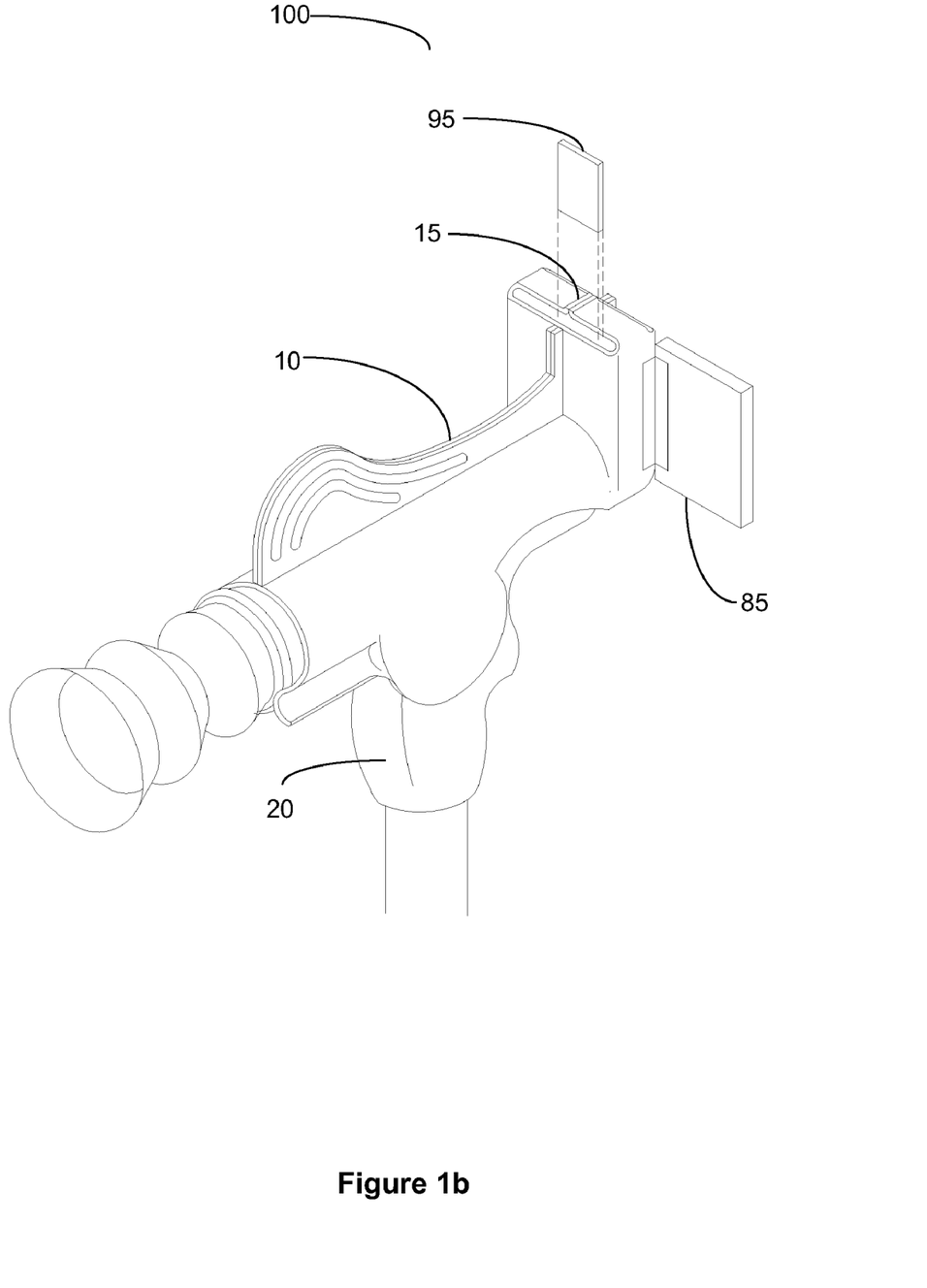
FIG. 1b illustrates a perspective view of a second exemplary embodiment of an ophthalmological diagnostic system with a memory card and viewing screen.

FIG. 1b illustrates a perspective view of a second exemplary embodiment of ophthalmological diagnostic system 100. In the embodiment shown, optical communication housing 10 includes viewing screen 85, which allows the user to view the same image as digital camera 30 and ophthalmoscope 20, and memory card 95, for storing acquired photographs and video.

In the embodiment shown, viewing screen 85 is secured to the edge of housing a hinge, allowing it to fold inward when not in use, while memory card 95 is inserted into a slot in the top of optical communication housing 10. In other embodiments, viewing screen 85 and memory card 95 may be positioned elsewhere on optical communication housing 10. For example, viewing screen 85 may protrude from the top of optical communication housing 10 or be located on the back of optical communication housing 10, and memory card 95 may be inserted into a slot in the side of optical communication housing 10.

In the embodiment shown, ophthalmological diagnostic system 100 does not require USB cable 55 for connecting digital camera 30 to computer 50 (not shown) as viewing screen 85 and memory card 95 may be used to view and store any acquired images and/or video.

Figure 1C:
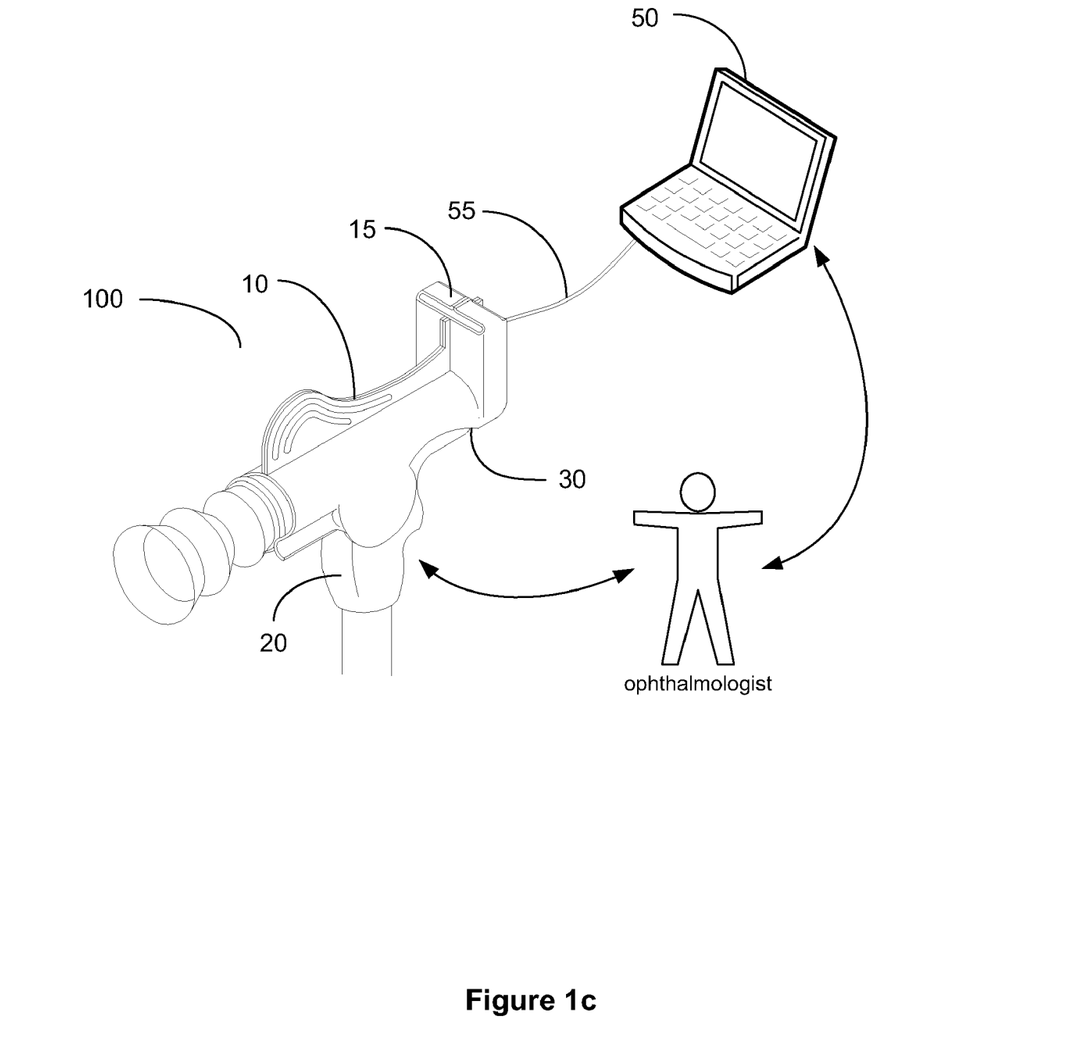
FIG. 1c illustrates a perspective view of an exemplary embodiment of an ophthalmological diagnostic system directly connected to a computer.

FIG. 1c illustrates a perspective view of an exemplary embodiment of ophthalmological diagnostic system 100. In the embodiment shown, digital camera 30 is connected to computer 50 via USB cable 55. The image viewed by ophthalmoscope 20 is captured by digital camera 30 in the form of a photograph or video and displayed on the screen of computer 50. To capture the image as a photograph or as a video, snapshot button 15 on optical communication housing 10 is pressed or digital camera 30 is activated by another means, such as by voice, foot pedal, key stroke, mouse click, or touch screen.

Ophthalmological diagnostic system 100 allows the image viewed through ophthalmoscope 20 to be captured. The images and/or video may be saved in the patient's file so that changes may be monitored over time, forwarded to a diagnostician for a consult, shown to a minor patient's parents, or used for patient education or another purpose. In various embodiments, ophthalmological diagnostic system 100 is ADA complaint. For example, ophthalmological diagnostic system 100 allows the ophthalmologist, optometrist, or other user to communicate with a deaf individual using the images/video captured using ophthalmological diagnostic system 100.

In the embodiment shown, an ophthalmologist is using ophthalmological diagnostic system 100; however, the ability to capture images and/or video and forward them to an ophthalmologist for diagnosis makes ophthalmological diagnostic system 100 ideal for use by non-ophthalmologists and non-optometrists (e.g., emergency room doctors, military doctors). In addition, the portability of ophthalmological diagnostic system 100 makes it ideal for out-of-office visits and other settings where traditional ophthalmological camera equipment is not readily available, such as third-world countries, remote areas, combat zones, at sea, and in space.

Figure 2:
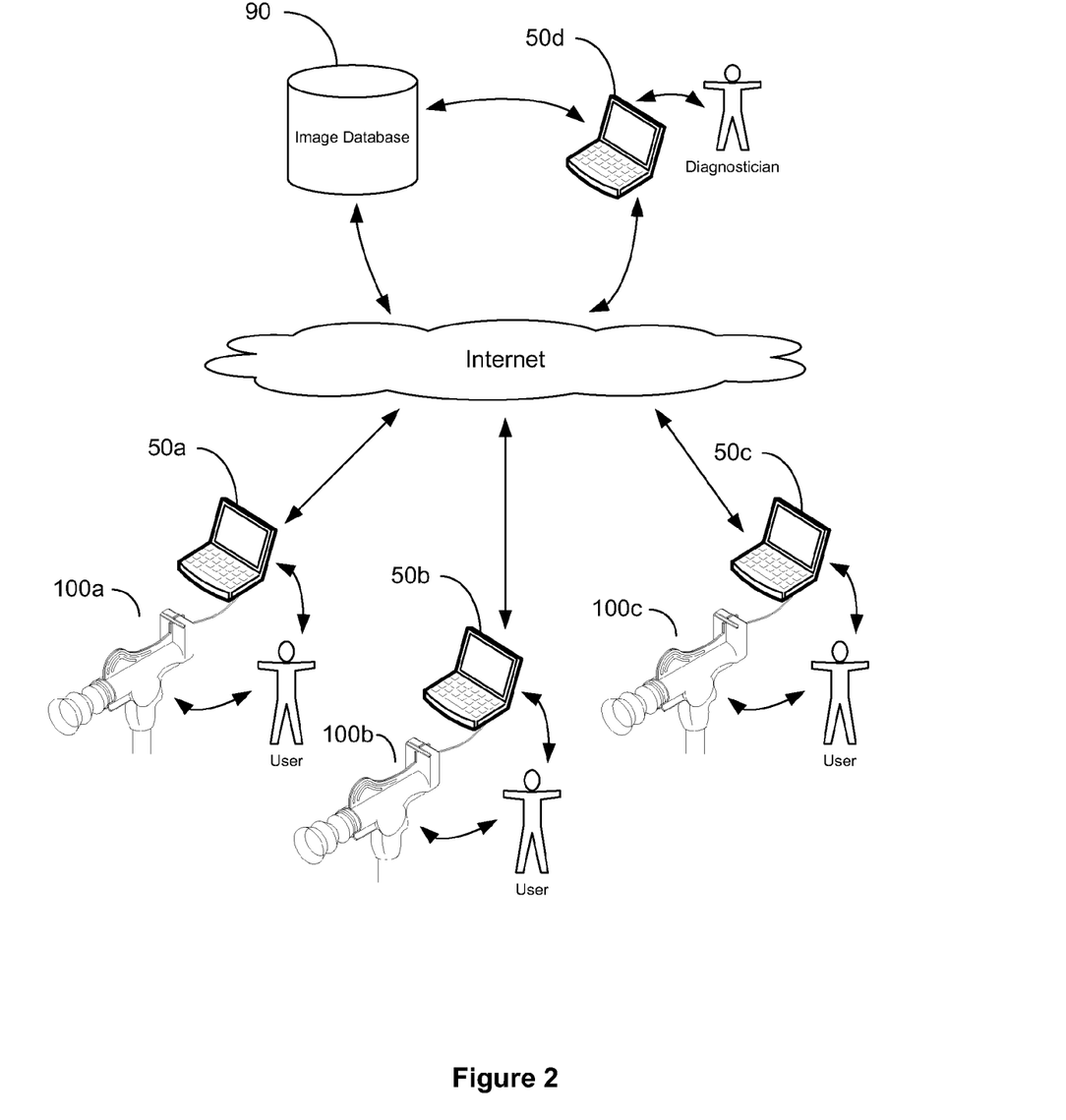
FIG. 2 illustrates an exemplary embodiment of a plurality of ophthalmological diagnostic systems with a diagnostician at a remote location.

FIG. 2 illustrates an exemplary embodiment of ophthalmological diagnostic systems 100a, 100b, 100c wirelessly connected to image database 90. In the embodiment shown, ophthalmological diagnostic systems 100a, 100b, 100c are wirelessly connected to image database 90, which stores images and videos acquired by the user of ophthalmological diagnostic systems 100a, 100b, 100c. The images and videos may be wirelessly transmitted from image database 90 to computer 50d where they can be viewed and analyzed by a diagnostician, allowing a single diagnostician to be able to remotely view and analyze images and/or videos from multiple locations and users.

In an exemplary embodiment, images and videos are labeled and stored in image database 90 in a HIPAA compliant manner. For example, image database 90 will allow only authorized individuals to view the images and videos and will prevent the images and videos from being altered and resaved. In various embodiments, image database 90 may further compile statistical information for educational purposes.

Figure 3:
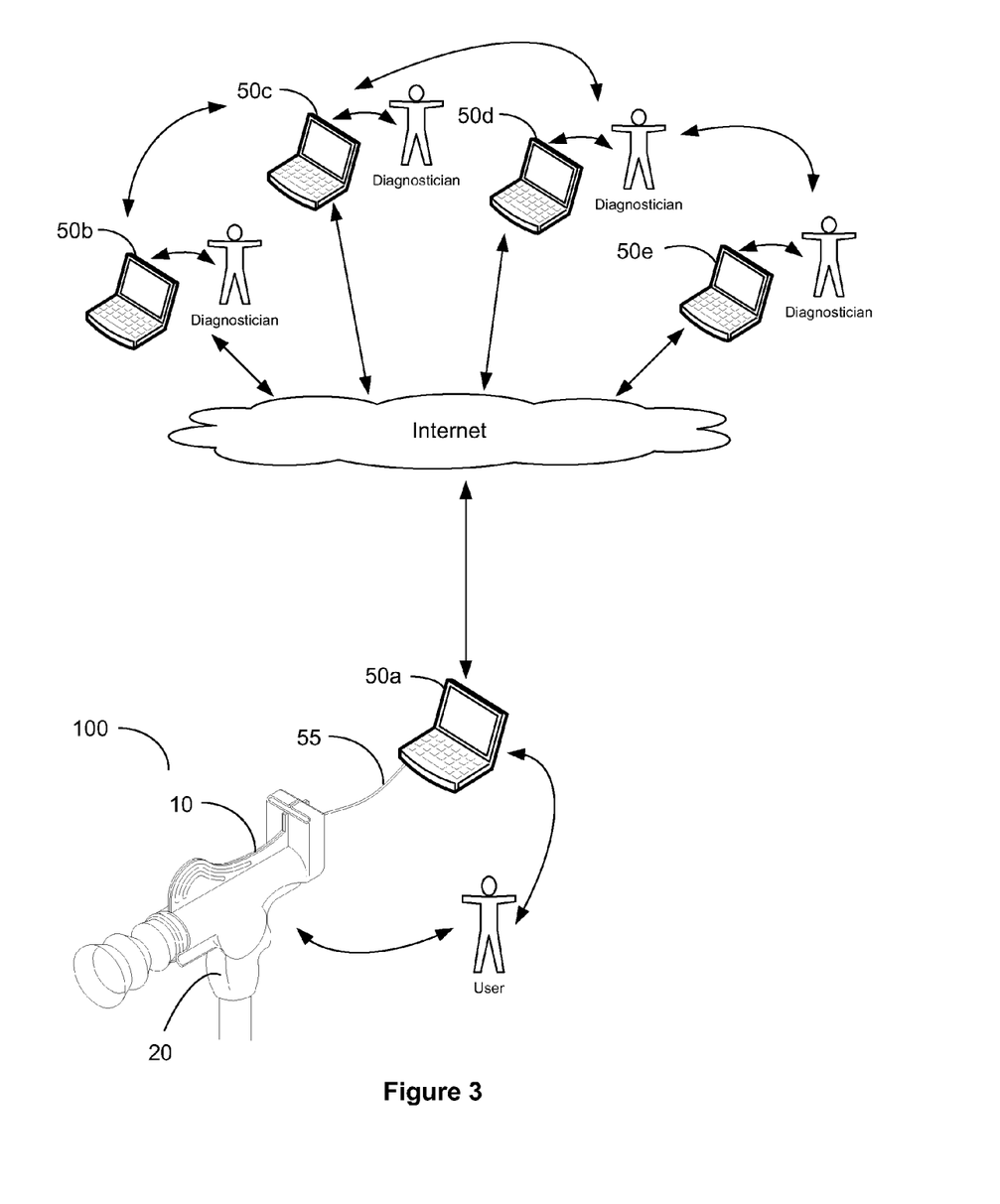
FIGS. 3 and 4 illustrate exemplary embodiments of an ophthalmological diagnostic system with a plurality of diagnosticians at remote locations.

FIG. 3 illustrates an exemplary embodiment of ophthalmological diagnostic system 100 connected to computer 50a via USB cable 55 and computer 50a is wirelessly connected to computers 50b, 50c, 50d, 50e. In the embodiment shown, the user of ophthalmological diagnostic system 100 is a non-diagnostician. The images and/or video captured by the user are wirelessly transmitted to computers 50b, 50c, 50d, 50e where the images and/or video can be viewed and analyzed by a diagnostician and the condition diagnosed, facilitating collaboration among the user and one or more ophthalmologists. In an exemplary embodiment, one or more ophthalmologists can wirelessly transmit information back to computer 50a where it can be viewed by the user.

In other embodiments, the user of ophthalmological diagnostic system 100 may be an ophthalmologist, optometrist, or another individual trained to analyze and identify conditions of the eye.

In the embodiment shown, computer 50a is wirelessly connected to four computers and four diagnosticians; however, in other embodiments, computer 50a may be wirelessly connected to any number of computers and/or images/video may be received by any number of individuals.

In various embodiments, one or more of the diagnosticians viewing the images and/or video from a remote location may be able to control the software on computer 50*a* and/or ophthalmoscope 20 in order to obtain the views necessary for analysis and diagnosis.

Figure 4:
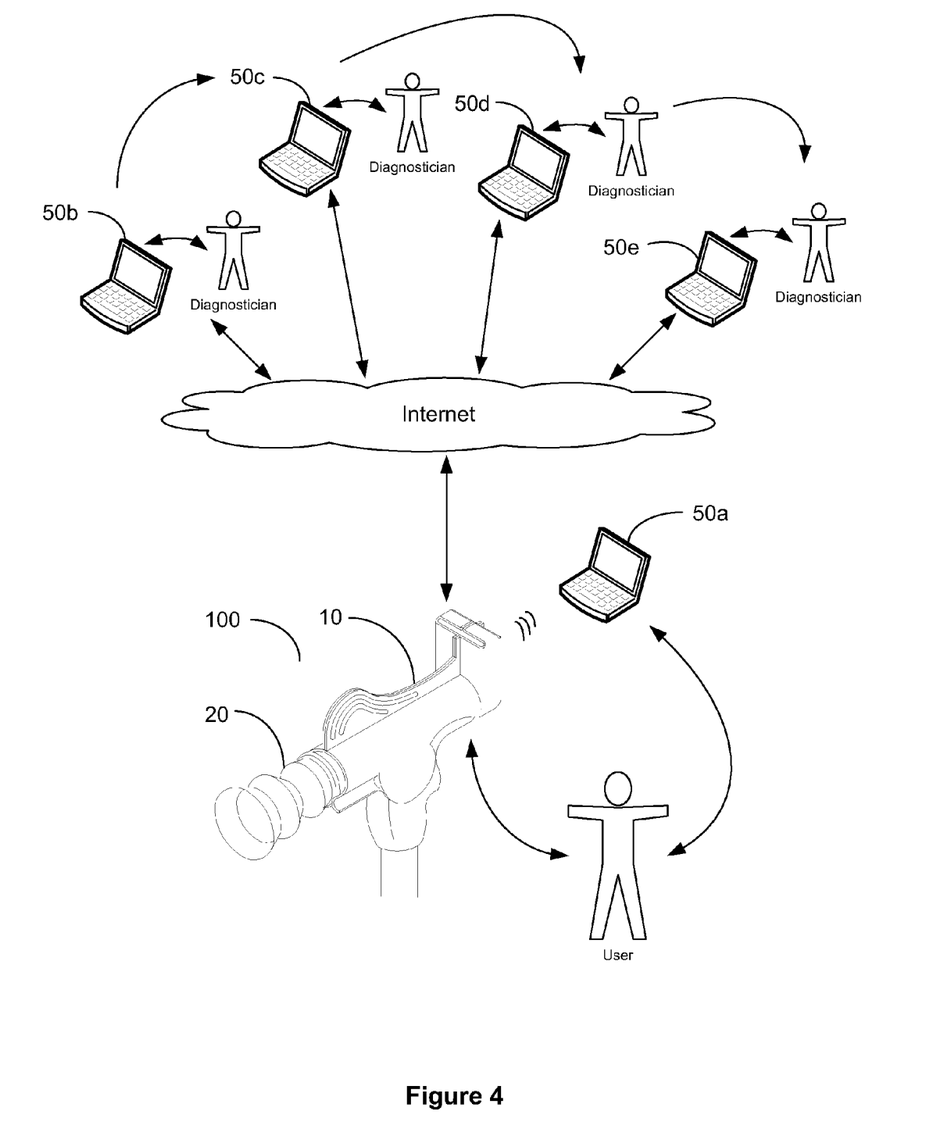

FIG. 4 illustrates an exemplary embodiment of ophthalmological diagnostic system 100 wirelessly connected to computers 50*a*, 50*b*, 50*c*, 50*d*, 50*e*. In various embodiments, ophthalmological diagnostic system 100 includes a wireless card, allowing information to be wirelessly transmitted to one or more devices.

Figure 5:
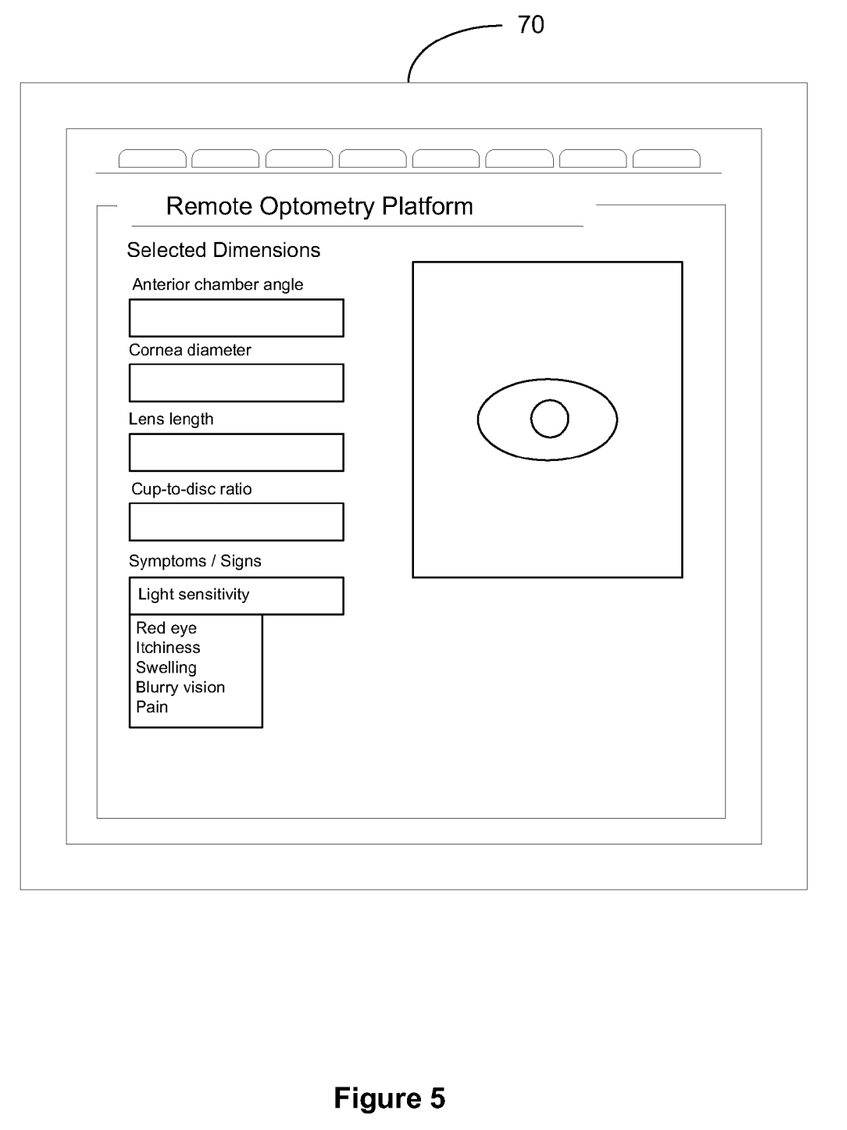
FIG. 5 illustrates an exemplary embodiment of a computer interface for an ophthalmological diagnostic system.

FIG. 5 illustrates an exemplary embodiment of computer interface 70 for ophthalmological diagnostic system 100. In the embodiment shown, interface 70 includes an image field, a plurality of text fields, and a drop down menu for selecting one or more symptoms. The text fields (e.g., anterior chamber angle, cornea diameter, lens length, cup-to-disc ration) allow the diagnostician to input one or more dimensions, which may be relevant to diagnosis. For example, cup-to-disc ratio compares the diameter of the cup portion of the optic disc with the total diameter of the optic disc, and is an important measurement for assessing the progression of glaucoma.

In an exemplary embodiment, computer interface 70 allows a user to view, save, and label images and videos, capture a still image from a video, as well as input diagnostic information and patient communication. In various embodiments, computer interface 70 may include a series of questions and/or user and may have additional functions, such as tracking individuals who have viewed the information, listing of potential treatment options, and/or providing a searchable image database for comparing the obtained images and/or videos with other images.

In another exemplary embodiment, computer interface 70 may have fields or be configured to allow a user to track, enter, or select signs and systems. The signs and symptoms may be correlated with a database which assists in diagnostics. For example, a corneal staining could be due a scratch or injury. But if other signs and symptoms (e.g., a rash on the nose, watering, burning, or tingling) are present, they could indicate that the appropriate diagnosis is not a scratch but rather a herpetic infection. Treating a patient for a scratch with steroids, rather than identifying herpes, causes hundreds of cases of blindness each year. (An estimated 400,000 individuals in the United States have had some form of ocular herpes. Each year, nearly 50,000 new and recurring cases are diagnosed in the United States.) Herpes simplex is the most common infectious cause of corneal blindness in the United States.

In another embodiment, software may be used to grade diabetic retinopathy.

In various embodiments, ophthalmological diagnostic system 100 utilizes advanced image analysis software with advanced graphical capabilities that allows the diagnostician to sample and test pixels to search for variants in the eye when a higher resolution image is not available and/or when visual inspection is not sufficient.

Figure 6:
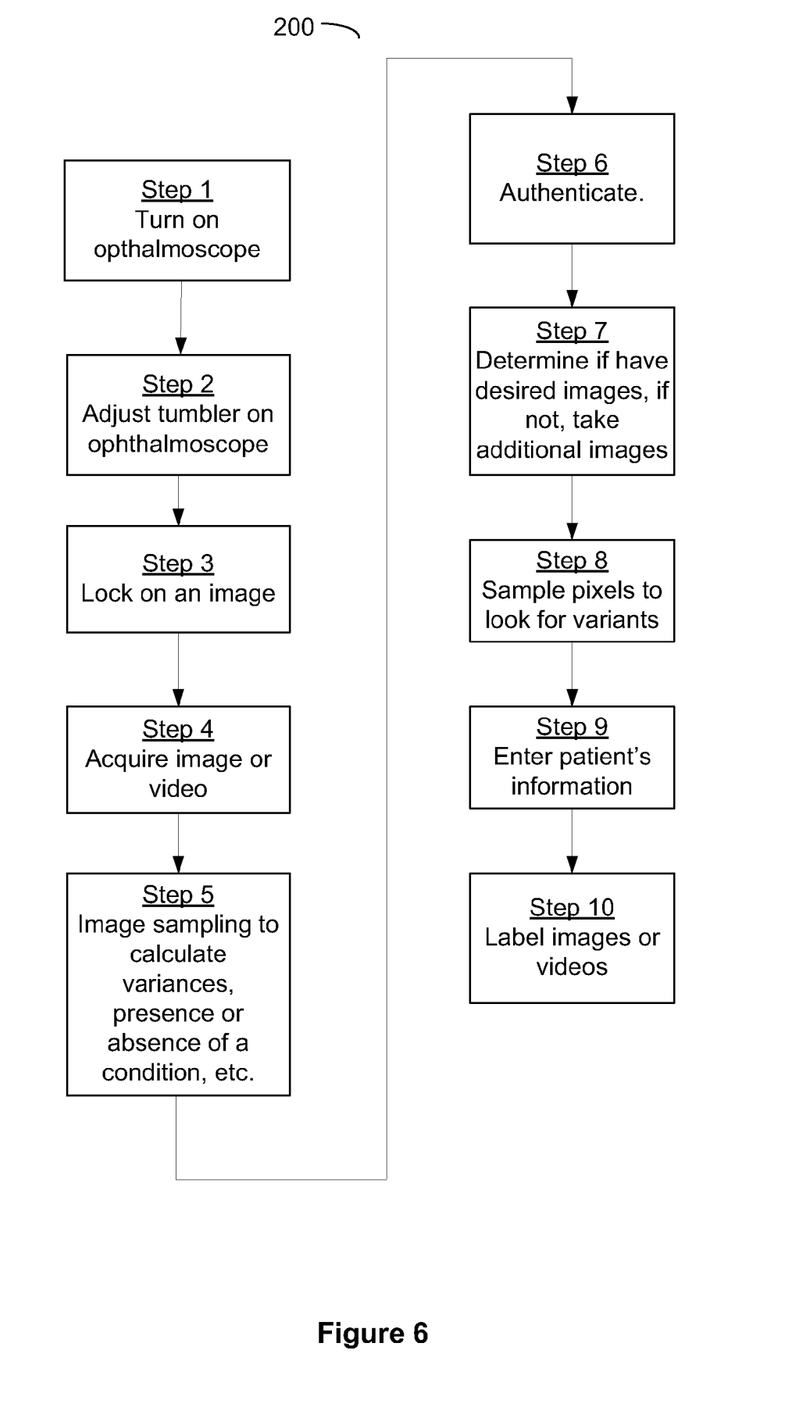
FIG. 6 illustrates an exemplary embodiment of a method of using an ophthalmologic diagnostic system.

FIG. 6 illustrates an exemplary embodiment of method 200 for using an ophthalmologic diagnostic system. In step 1, the user turns on ophthalmoscope 20 and in step 2, the user adjusts the variable focus tumbler on ophthalmoscope 20 to focus on the desired portion of the eye. For example, to look at the back of the eye, the user will leave the tumbler at zero or move the tumbler downward; to focus on the front of the eye, the user will move the tumbler upward.

In step 3, the user locks on a desired portion of the eye. The image viewed by ophthalmoscope 20 and digital camera 30 is displayed on computer 50. In step 4, the user presses snapshot button 15 on optical communication housing 10 to acquire the image or video, which may selected on computer interface 70.

In step 5, the user may sample the captured images/videos to calculate variances, the presence or absence of a condition, or any other measurement or observation desired. In steps 6 and 7, the images/videos are authenticated and the user determines if the desired images/videos have been acquired. If not, additional images/videos are acquired.

In step 8, if visual inspection is not sufficient, the diagnostician utilizes image analysis software to sample and test pixels or to enhance the image to search for variants, which may identify one or more conditions. In steps 9 and 10, the patient's information is entered, and the images/videos labeled.

In other embodiments, the steps of method 200 vary and are dependent on the particular circumstances (e.g., the location, the patient's condition) as well as the training and education level of the user and diagnostician.

The images and videos captured using ophthalmological diagnostic system 100 provide the user or a remote diagnostician with a comprehensive visual image of the eye. The ability to capture a video, in addition to a still image, provides binocularity and motion parallax, allowing the diagnostician to determine the depth and elevation of various portions of the eye. In various embodiments, a plurality of still images may be combined to create a stereoscopic or three-dimensional image of the eye.

A comprehensive visual image of the eye can reveal innumerable ocular and systematic traumas and conditions of the eye lid (e.g., blepharitis, herpes zoster, herpes simplex, madarosis, poliosis, pediculosis, chalazions, hordeolums, contact dermatitis, ptosis, dermatochalasis, ectropion, entropion, trichiasis, bell's palsy, floppy eyelid syndrome, tumors, nevi, papillomas, cysts, hemangiomas, malignancies, neurofibromatosis, dacryocyctitis, and dacryostenosis); conjunctiva (e.g., foreign bodies, subconjunctival hemes, dry eye, chemosis, follicles, papilla, hyperemia/injection, phlyctenule, lymphatic cysts, conjunctivitis—viral, bacterial, or allergic (ocular like GPC or systemic like Chlamydia), episcleritis, scleritis (autoimmune issues, HLA-B27), and malignancies); cornea (e.g., abrasions, foreign bodies, ulcers, recurrent erosions, thermal burns, chemical burns, infections/keratitis (bacterial, fungal, parasitic, viral), dellen, SPK, edema, pannus, arcus senilis, keratopathy, degenerations, keratoconnus, Fuch's dystrophy, Wilson's Disease, and corneal neo); anterior chamber and iris (e.g., angle estimates, hyphema, cells/flare (anterior chamber reaction), KP's uveitis/iritis, cyclodialysis, colobomas, rubeosis (DM), anisocoria, Adies tonic pupil, Argyll Robertson pupil, Horner's syndrome, and iris nodules (NF); lens (e.g., cataracts, exfoliation, and lens dislocation); vitreous (e.g., floaters, posterior vitreal detachments, hemorrhages, asteroid hyalosis); macula and retina (e.g., hemorrhages, artery occlusions, vein occlusions, diabetic retinopathy, hypertensive retinopathy, macular degeneration (ARMD), vitreal maculopathies, central serous, macular edema, epiretinal membranes, myelination, drug maculopathies, retinal detachments, posterior uveitis, nevi, malignancies, CHRPEs peripheral degenerations, retinitis pigmentosa, albinism, benign retinal tumors, and congential malformations/colobomas); and optic nerve (e.g., optic neuritis (MS), glaucoma, and optic neuropathies).

Figure 7:
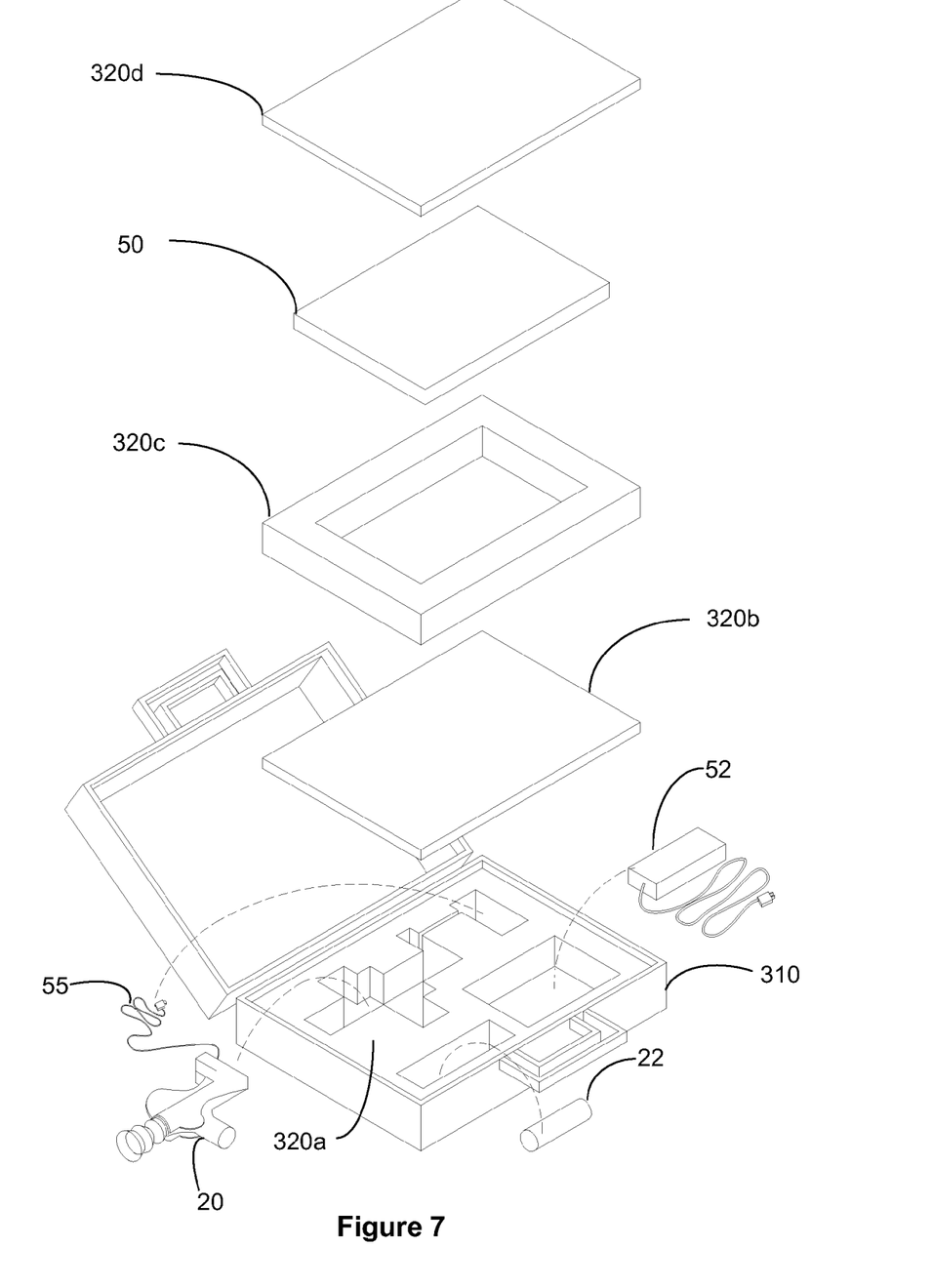
FIG. 7 illustrates an exemplary embodiment of an ophthalmological diagnostic system kit.

FIG. 7 illustrates an exemplary embodiment of ophthalmological diagnostic system kit 300. In the embodiment shown, ophthalmological diagnostic system kit 300 is comprised of case 310 and padding 320*a*, 320*b*, 320*c*, 320*d*. To assemble kit 300, padding 320*a* is placed inside case 310. In the embodiment shown, padding 320a contains cavities for optical communication housing 10 secured to ophthalmoscope 20, ophthalmoscope power supply 22, USB cable 55, and power cord 52 for computer 50. When the components are positioned in the designated cavities, padding 320b is placed on top of the components. Padding 320c is then placed on top of padding 320b and computer 50 is placed inside the cavity in padding 320c. Padding 320d is positioned on top.

In various other embodiments, diagnostic system kit 300 may contain any number of layers of padding and or be designed to fit in a larger, smaller, or differently sized case.

What is claimed is:

1. A ophthalmological diagnostic system comprised of:
a tubular optical communication housing for securing a digital camera in optical communication with a direct ophthalmoscope having a field of view of 6.5 to 60 degrees and free from of any reflective device, wherein said tubular optical communication housing defines a hollow direct ophthalmoscope head receiving channel having an internal diameter;
a digital camera;
a direct ophthalmoscope having a single barrel tubular head with an external diameter less than said internal diameter and a monocular viewing optic;
an image viewing means for viewing an image seen by said direct ophthalmoscope and said digital camera, wherein said image viewing means is selected from the group consisting of a computer screen, laptop screen, tablet computer screen, viewing screen, touch screen, projection screen, television screen, and a mobile phone screen,
wherein said image viewing means is connected to said digital camera by a connection selected from the group consisting of a USB cable and a wireless connection;
a camera activating means, wherein said camera activating means is selected from a group consisting of a button, voice, foot pedal, key stroke, mouse click, and a touch screen; and
a storage component for storing said captured image.

2. The system of claim 1 wherein said digital camera is secured inside said tubular optical communication housing.

3. The system of claim 1 wherein said tubular optical communication housing is comprised of two reciprocal housing members having contours which conform to the dimensions of said direct ophthalmoscope and further includes engagement components to join said housing members.

4. The system of claim 1 wherein said tubular optical communication housing further includes an upright grasping component for removing said tubular optical communication housing from said direct ophthalmoscope.

5. The system of claim 1 wherein said camera activating means is a button.

6. The system of claim 1 wherein said captured image is selected from a group consisting of a photograph and a video.

7. The system of claim 1 wherein said storage component is selected from a group consisting of a computer hard drive, database, memory card, flash drive, and an external hard drive.

8. The system of claim 1 which further includes a user interface.

9. The system of claim 1 which further includes a software component having a user interface with diagnostician prompts.

10. The system of claim 1 which further includes a software component with image sampling capabilities.

11. The system of claim 1 which further includes a software component with filters.

12. The system of claim 1 which further includes a software component capable of associating image data with known medical conditions.

13. The system of claim 1 which further includes a software component capable of adjusting image data for enhanced viewing.

14. The system of claim 1 which further includes a software component capable of enhancing the resolution of an image.

15. The system of claim 1 which further includes the capability for a user to be in communication with a diagnostician in real time.

16. The system of claim 1 which further includes a software component and user interface for correlating signs and symptoms entered into said user interface with a database of known conditions associated with said signs and symptoms.

17. The system of claim 16 wherein said known conditions are selected from a group consisting of measurable variations in the physiology of the eye.

* * * * *